United States Patent [19]

Simon

[11] Patent Number: 4,986,501
[45] Date of Patent: Jan. 22, 1991

[54] EQUIPMENT CARRIER

[75] Inventor: Peter Simon, Munich, Fed. Rep. of Germany

[73] Assignee: KNURR-Mechanik fur die Elektronik Aktiengesellschaft, Munich, Fed. Rep. of Germany

[21] Appl. No.: 321,862

[22] Filed: Mar. 10, 1989

[30] Foreign Application Priority Data

Mar. 11, 1988 [DE] Fed. Rep. of Germany ....... 3808223

[51] Int. Cl.$^5$ .......................... G09G 1/00; A47B 91/00
[52] U.S. Cl. .................................. 248/122; 248/130; 248/920; 248/923; 108/148; 108/6
[58] Field of Search ............... 248/122, 129, 130, 133, 248/291, 920, 922, 923; 108/106, 148, 144, 6, 1

[56] References Cited

U.S. PATENT DOCUMENTS 1,689,626 10/1928 Gallowitz ........................... 108/6 X
1,814,342 7/1931 Smith ................................. 248/129
3,606,450 9/1971 Sedgwick ............................ 108/6
3,640,228 2/1972 Busse ................................... 108/6
3,641,846 2/1972 Charnay .............................. 108/6
4,616,218 10/1986 Bailey et al. .................... 248/920 X

FOREIGN PATENT DOCUMENTS 8501648 4/1985 World Int. Prop. O. .......... 248/922

Primary Examiner—Karen J. Chotkowski
Attorney, Agent, or Firm—Beveridge, DeGrandi & Weilacher

[57] ABSTRACT

An equipment carrier, e.g. for a monitor or measuring device and having a mounting plate is described, which is tilt-adjustable and lockable in different tilt angles. The equipment carrier comprises a base frame mounted on runners and on which are arranged two columns. A mounting plate is vertically adjustably suspended by means of two oscillating arms between the two columns.

16 Claims, 2 Drawing Sheets

4,986,501

EQUIPMENT CARRIER

BACKGROUND OF THE INVENTION

The invention relates to an equipment carrier, e.g. for a monitor or measuring device, with a tilt-adjustable mounting plate which can be locked in different tilt angles.

Large numbers of equipment carriers or supports are used in laboratories and offices. They are normally used for receiving measuring equipment, indicators and display units. The tilt adjustability is possible through an ergonomically correct arrangement, i.e. the elements relevant for the operator or observer can be arranged with an optimum tilt or inclination.

The known equipment carriers are supported on a central column, to whose free end is articulated the mounting plate. Although such constructions can be used very satisfactorily in many cases, they are unsuitable, particularly for very heavy equipment, because they are insufficiently stable. There is a risk with heavy or large-volume equipments, that they will be unable to withstand the load, or that they can easily lose their balance.

SUMMARY OF THE INVENTION

The problem addressed by the invention is to provide an equipment carrier of the aforementioned type, which can also be loaded with heavy equipment, but is still adequately stable.

This problem is solved in that a heavy base frame with two vertical columns with a given spacing from one another is provided, that the mounting plate is located on two oscillating arms between the columns, and which are articulated to the latter and that the mounting plate can be locked with respect to its tilt on the columns.

The invention has the advantage that as a result of the two columns a reliable support of the mounting plate and equipment arranged thereon is ensured, while as a result of the heavy base frame, the center of gravity of the overall arrangement is at a low level. Due to the oscillating or pendulum suspension, the center of gravity of the equipment is below the pivot pin, so that the mounting plate or the equipment arranged thereon cannot assume a critical unstable position. Should the locking device be released by an operator and e.g. an incorrect manipulation take place, the mounting plate would automatically assume a stable position, without in any way prejudicing the arrangement of the equipment. In addition, the two columns constitute a lateral protection for the equipment, because they span the space over the mounting plate on two sides in much the same way as a guard bow.

According to a preferred development of the invention, the joints of the oscillating arms are vertically adjustably arranged on the columns. This is simply attainable in that in each case the joints surround horizontally positioned bolts serving as a pendulum axis and that said bolts are detachably fixed to the associated columns.

The bolts are preferably screwed to the columns. For continuous vertical adjustment purposes, the columns are provided with spacedly superimposed screw holes. In order to ensure a vertical adjustment, it can be appropriate to provide each column with a vertically directed fastening groove and for the bolts to be detachably clamped in said fastening groove. Thus, for vertical adjustment purposes, it is merely necessary to loosen the two bolts in such a way that they can be moved in the fastening grooves into the desired position, where they can be clamped again by tightening.

It is also advantageous that on the mounting plate is provided at least one bar deflectable at right angles to the pendulum axis for engaging on a column-side counterpart and with which the mounting plate can be locked under different tilt angles. Preferably there is a second locking device of this type, so that the base plate can be supported with respect to its inclination on both columns.

A particularly operationally reliable locking effect is achieved in that the bar counterpart is constructed as a perforated plate, in whose perforations engages the associated bar for continuous tilt adjustment.

The ease of operation is further increased in that the column-side bar counterpart is arranged on a support, which is connected in slide-proof manner with the associated bolt of the pendulum suspension.

In order to ensure that the oscillating movement is not impeded, it is appropriate to arrange the oscillating arms in a casing, which is constructed on the support. This measure also enables the equipment carrier to be given an attractive appearance.

It is appropriate to provide the casing front associated with the mounting plate with an opening and by means of which the free end of the particular oscillating arm can be led out to the mounting plate and through which the particular bar is passed into the casing for engaging in the counterpart. The opening can also limit the pendulum or oscillating stroke.

It is possible for the mounting plate to rotate about a vertical axis by providing the base frame with runners.

The mechanical loadability of the equipment carrier is also assisted in that the two facing supports are reciprocally supported below the mounting plate by means of a crossbeam. Thus, level with the equipment to be carried, both columns are transversely reinforced. Through the arrangement of the crossbeam on the supports, said transverse reinforcement is also obtained for each vertical adjustment without the operator having to do anything in this respect.

The forces occurring during a tilting or deflection of the mounting plate are preferably transferred to the columns in that the supports engage positively behind the columns at right angles to the oscillating direction and on two sides.

The operation of the two bars is facilitated in that they engage with a common operating lever, which is positioned on one front surface of the mounting plate. The two bars can be articulated in opposition through operating this lever.

It is also advantageous with regard to ease of operation that the bar operating lever is arranged within finger reach of a handle for the mounting plate. This offers the advantage that it is possible with one hand to both release the bar and also position the mounting plate in a controlled manner.

SHORT DESCRIPTION OF THE DRAWINGS

The invention is described in greater detail hereinafter relative to an embodiment and the attached drawings, which drawings show:

FIG. 1 Diagrammatically a side view of an equipment carrier in accordance with the present invention;

FIG. 2 Diagrammatically a front view of the equipment carrier according to FIG. 1;

FIG. 3 A plan view of an equipment carrier mounting plate; and

FIG. 4 Diagrammatically an exploded view showing in detail a portion of the equipment carrier of the present invention.

DESCRIPTION OF A PREFERRED EMBODIMENT

Figure 1:
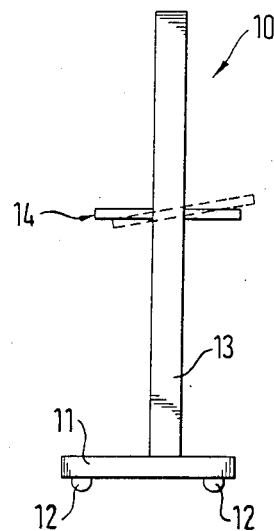
Figure 2:
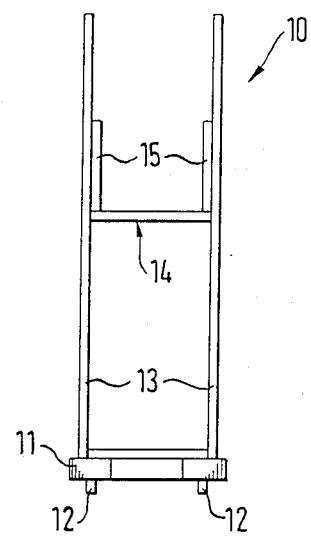

As illustrated in FIGS. 1 and 2, an equipment carrier or support designated overall by 10 comprises a base frame 11 with runners 12, by means of which the equipment carrier 10 is freely movable on a substrate, e.g. the floor. Two vertical columns 13 are given a predetermined spacing on base frame 11, so that a substantially fork-like arrangement is formed.

Between the two columns 13 a mounting plate 14 is suspended on two oscillating arms 15 (FIG. 2), which are pivotably articulated about a horizontal axis to the two columns 13. Mounting plate 14 can be inclined in an arbitrary manner by a deflection of the oscillating arms 15. FIG. 1 shows an inclined position in broken line form. Mounting plate 14 with oscillating arms 15 is vertically adjustably mounted over the entire length of the columns. The two drawings illustrate that fundamentally several such mounting plates 14, suspended on oscillating arms 15, can be arranged between the two columns 13. It is also possible to provide fixed shelves or the like between the columns 13. This makes it possible to form an equipment tower and columns 13 can be up to 2 m high. In order to ensure an adequate stability, the base frame 11 is made from cast metal and has a considerable weight. Therefore the center of gravity of the complete arrangement is relatively low, even if equipments (not shown) are arranged on the equipment carrier and also have a considerable weight.

Figure 3:
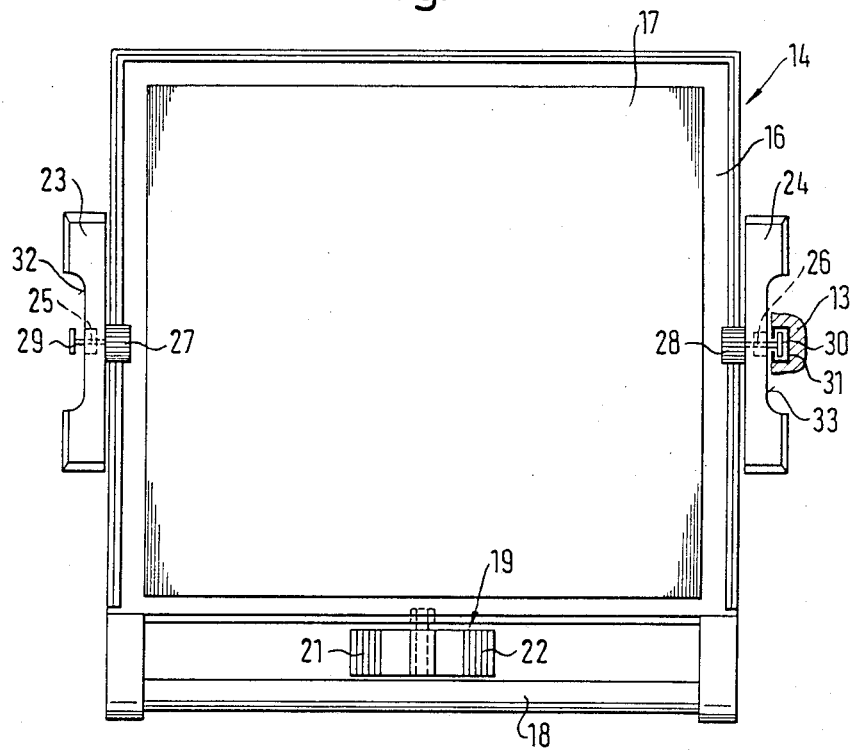

FIG. 3 is a plan view of the mounting plate 14 and its suspension. Mounting plate 14 extending in the plane of the drawing essentially comprises a metal frame 16 and a surface flush-terminating filling 17. On one front side, i.e. in the pivoting direction, is provided a rod-like handle 18, which extends with a predetermined spacing over the entire width of mounting plate 14. A centrally mounted, double-section operating mechanism 19 is positioned in the gap between handle 18 and mounting plate 14 and is used for operating a crossbar, which is described in detail relative to FIG. 4. The two sections 22, 21 can be deflected out of the drawing plane, in that the operator e.g. simultaneously secures or deflects the mounting plate 14 by means of the handle 18.

In the example shown in FIG. 3, the oscillating arms are in each case located in the interior of a support 23, 24, which is vertically adjustably screwed to the associated column. This takes place with the aid of a horizontally arranged bolt 25 or 26, on which bolts are also suspended the oscillating arms. The bolts 25, 26 are on the one hand provided with a knurled nut 28 operable from the outside and on the other hand with a head 29 or 30 for vertical adjustable engagement with, in each case, one vertically directed groove 31 in the associated column 13. So as not to overburden the drawing, a groove 31 is only shown on the right-hand side of FIG. 3 as a partial cross-section through the particular column 13. The statements made here also apply to the side with the bolt 25.

Groove 31 is provided with two L-legs engaging behind head 30. By rotating the knurled nut 28, bolt 26 with head 30 is fixed or detached with respect to the L-legs. As the groove 31 extends over the entire length of column 13, the mounting plate 14 can be moved into any random height and fixed there.

On the column side, supports 23, 24 are provided with a half-open recess 32, 33 extending in the direction of the columns and which positively surrounds the associated columns 13. In FIG. 3 recesses 32, 33 are at right angles to the drawing plane, i.e. as a result of the self-closure they are fixed with respect to a movement in the drawing plane, particularly in the pivoting direction of mounting plate 14.

Figure 4:
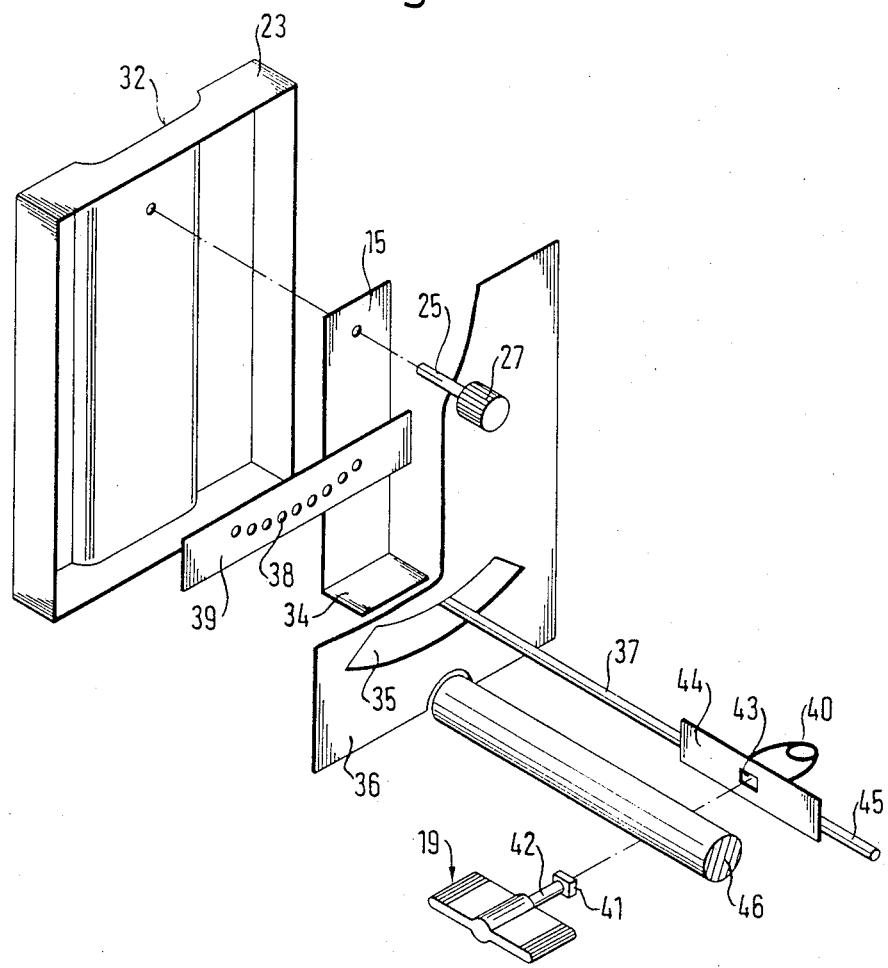

FIG. 4 shows the way in which the support 23 and the associated oscillating arm 15 are suspended by means of bolt 25. Support 23 is shaped as a casing, in which the oscillating arm 15 is displaceable. At its free end oscillating arm 15 is provided with an abutment 34 to which is fixed the mounting plate 14. Abutment 34 is passed to the outside through an opening 35 in a casing cover 36. Thus, opening 35 also serves as a boundary for a pivoting or oscillating movement.

Through opening 35 is also passed a crossbar 37, which is mounted on the mounting plate, which is not shown in this drawing. Its free end detachably passes into one of the holes 38 in a plate-like bar counterpart 39, which is fixed to support 23. Mounting plate 14 can be locked with different deflections or inclinations with the aid of the crossbar 37 and holes 38.

In the example shown here, bar 37 is biased by means of a spring clip 40, so that it automatically engages in one of the holes 38. It is deflected or displaced with the aid of a cam 41 on pivot pin 42 of operating mechanism 19. Cam 41 engages in a correspondingly shaped recess 43 on a control plate 44 of bar 37.

In the extension of crossbar 37 is provided a further crossbar 45, which cooperates with an identical, but mirror-inverted arrangement located in the interior of support 24 (FIG. 3).

The two crossbars 37, 45 and the associated components are located below guide 17 (FIG. 3) and can be covered at the bottom. Below the mounting plate a crossbeam 46 passes between the two supports 23, 24 and reciprocally supports the same.

What we claim is:

1. An equipment carrier comprising: a tilt-adjustable mounting plate lockable at different tilt angles; a base frame; two vertical columns connected to the base frame; two oscillating arms for positioning the mounting plate between the columns, the oscillating arms being articulated to the columns by horizontal oriented bolts and the mounting plate being lockable at different tilt angles with respect to the columns; said carrier further including joints permitting vertical adjustment of the oscillating arms on the columns, the joints comprising the horizontally oriented bolts which provide a pendulum axis, each column further including a vertically oriented fastening groove for receiving the bolts therein, the bolts being attachable to the columns in the grooves to fix the arms vertically with respect to the columns and detachable to permit movement of the arms in a longitudinally displaceable manner along the fastening grooves; the mounting plate being provided with a first crossbar that is deflectable in a line parallel to the pendulum axis; said carrier further including a perforated plate having holes for engagement with the first crossbar to provide for continuous tilt adjustment; the center of gravity of the equipment carrier being below the bolts such that the carrier cannot assume a critical unstable position.

2. An equipment carrier according to claim 1, wherein the bolts are screwed to the columns.

3. An equipment carrier according to claim 1, wherein the mounting plate is provided with a second crossbar that is deflectable in a line parallel to the pendulum axis for engaging on a column-side bar counterpart with which the mounting plate can be locked under different tilt angles.

4. An equipment carrier according to claim 3, wherein the bar counterpart is constructed as a perforated plate, in whose holes engage the second crossbar for continuous tilt adjustment.

5. An equipment carrier according to claim 4, wherein the two crossbars engage with a common operating mechanism located on one front surface of the mounting plate.

6. An equipment carrier according to claim 1, wherein the base frame is provided with runners.

7. An equipment carrier comprising: a tilt-adjustable mounting plate lockable at different tilt angles; a base frame; vertical columns providing a given reciprocal spacing; two oscillating arms for locating the mounting plate between the columns, the oscillating arms each being arranged in a casing which is constructed on a support, the oscillating arms being articulated to the columns, the mounting plate being lockable at tilt angles with respect to the columns, the mounting plate being provided with at least one bar that is deflectable in a line parallel to a pendulum axis for engaging on a column-side bar counterpart, the bar and the bar counterpart allowing the mounting plate to be locked at different tilt angles.

8. An equipment carrier according to claim 7, wherein the bar counterpart is arranged on said support which is connected in slide-proof manner with an associated bolt to provide a pendulum suspension.

9. An equipment carrier according to claim 7, wherein a casing front which faces the mounting plate is provided with an opening through which the free end of the oscillating arm is passed to the mounting plate and through which said bar is passed into the casing for engaging in the bar counterpart.

10. An equipment carrier according to claim 7, wherein the supports positively engage behind the columns on two sides and at right angles to the oscillating direction.

11. An equipment carrier according to claim 7, wherein the two facing supports are reciprocally supported with a crossbeam below the mounting plate.

12. An equipment carrier comprising: a tilt-adjustable mounting plate lockable at different tilt angles; a base frame; vertical columns providing a given reciprocal spacing; two oscillating arms for locating the mounting plate between the columns, the oscillating arms being articulated to the columns and the mounting plate being lockable at tilt angles with respect to the columns; the carrier further including at least one crossbar and a column-side bar counterpart provided for the mounting plate, the at least one crossbar being deflectable in a line parallel to a pendulum axis for engaging with the column-side bar counterpart to allow the mounting plate to be locked at different tilt angles, wherein the at least one crossbar engages with a common operating mechanism located on one front surface of the mounting plate, the operating mechanism being located in finger reach of a handle for the mounting plate.

13. An equipment carrier according to claim 12, wherein the operating mechanism comprises a pivot pin, two sections arranged on the pivot pin, a cam on the pivot pin, said pivot pin being operable by deflecting the sections.

14. An equipment carrier according to claim 13, wherein the cam engages in a correspondingly shaped recess on a control plate on the crossbars.

15. An equipment carrier according to claim 14, wherein supports are provided with a half-open recess extending in the direction of the respective columns and positively surrounding an associated column.

16. An equipment carrier according to claim 12, wherein the operating mechanism is positioned in a gap between the mounting plate and a rod-like handle.

* * * * *